(12) United States Patent
Waksman et al.

(10) Patent No.: US 6,355,055 B1
(45) Date of Patent: Mar. 12, 2002

(54) ENDOVASCULAR SUPPORT DEVICE AND METHOD OF USE

(75) Inventors: Ron Waksman; Spencer B. King, III; Neal A. Scott, all of Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 08/967,331

(22) Filed: Oct. 21, 1997

Related U.S. Application Data

(63) Continuation of application No. 08/522,712, filed on Sep. 1, 1995, now abandoned.

(51) Int. Cl.⁷ .................................................. A61F 2/06
(52) U.S. Cl. ................... 623/1.13; 623/1.39; 623/1.42; 623/1.44; 623/1.41; 600/36
(58) Field of Search ............................ 623/1.12, 1.13, 623/1.39, 1.42, 1.43, 1.44, 1.41, 1.47; 600/36

(56) References Cited

U.S. PATENT DOCUMENTS

| | | |
|---|---|---|
| 4,345,340 A | 8/1982 | Rosen |
| 4,388,735 A | 6/1983 | Ionescu et al. |
| 4,470,157 A | 9/1984 | Love |
| 4,477,930 A | 10/1984 | Totten et al. |
| 4,629,459 A | 12/1986 | Ionescu et al. |
| 4,655,773 A | 4/1987 | Grassi |
| 4,687,483 A | 8/1987 | Fisher et al. |
| 4,729,139 A | 3/1988 | Nashef |
| 4,733,665 A | 3/1988 | Palmaz |
| 4,753,652 A | 6/1988 | Langer et al. |
| 4,759,758 A | 7/1988 | Gabbay |
| 4,969,896 A | 11/1990 | Shors |
| 5,147,514 A * | 9/1992 | Mechanic ............... 204/157.68 |
| 5,163,953 A | 11/1992 | Vince |
| 5,163,955 A | 11/1992 | Love et al. |
| 5,263,992 A | 11/1993 | Gruire |
| 5,383,927 A | 1/1995 | De Goicoechea et al. |
| 5,383,928 A | 1/1995 | Scott et al. |
| 5,387,236 A | 2/1995 | Noishiki et al. |
| 5,399,352 A | 3/1995 | Hanson |
| 5,413,597 A | 5/1995 | Krajicek |
| 5,449,382 A | 9/1995 | Dayton |
| 5,509,932 A | 4/1996 | Keogh et al. |
| 5,693,085 A * | 12/1997 | Buirge et al. ............... 623/1.12 |
| 6,187,038 B1 * | 2/2001 | Sullivan et al. ............ 623/1.43 |

* cited by examiner

Primary Examiner—Corrine McDermott
Assistant Examiner—Choon P. Koh
(74) Attorney, Agent, or Firm—Needle & Rosenberg, P.C.

(57) ABSTRACT

An endovascular support device adapted for local delivery of a therapeutic agent and for minimizing the rate of restinosis having a cylindrical support body with an inside surface and an opposite outside surface, and at least one layer of pericardial tissue covering at least a portion of at least a selected one of the inside surface or the outside surface of the cylindrical support body. At least one therapeutic agent is disposed on a portion of the support device.

28 Claims, 2 Drawing Sheets

LEGEND:

ENDOVASCULAR SUPPORT DEVICE AND METHOD OF USE

This application is a continuation of application Ser. No. 08/552,712, filed Sep. 1, 1995, which status is abandoned.

FIELD OF THE INVENTION

The present invention relates to the field of endovascular support to maintain patency of narrowed vessels and facilitate repair of injured or degenerated vessels by implantation of a device within the target vessel. More specifically, the invention relates to acceptable biological coverings for an endovascular support device and the local delivery of a therapeutic substance into the vascular tissue, as a complementary treatment.

BACKGROUND OF THE INVENTION

Partial and even complete blockage of the vascular system by the formation of an atherosclerotic plaque is a well known and frequent medical problem. Such blockages are often treated with percutaneous transluminal coronary angioplasty (PTCA), also known as balloon angioplasty, or by intravascular stent implantation. PTCA is an alternative to vascular bypass surgery, which includes a surgically exposing incision, and removing, replacing, or bypassing the defective blood vessel. Structures which have previously been used as intraluminal vascular grafts have included coiled stainless steel springs, and grafted stents made out of synthetic material (Dacron or PTFE). Examples of such prior art devices may be found in U.S. Pat. Nos. 5,306,286; 5,026,377; 5,019,085; 5,019,090; 4,913,141; 4,886,062; 4,733,665; and 4,503,569.

In balloon dilatation of vascular stenosis, or blockages, the balloon is inflated within the stenosed vessel, in order to shear and disrupt the wall component of the vessel to obtain an enlarged lumen. This may create a flap or tear at the intima or the media of the vessel wall. The intimal flap can fold down into the lumen and may occlude the vessel. Such occurrences contribute to the high incidence of restenosis which is prevalent. Currently, conventional balloon angioplasty is followed by roughly a 30% to 50% incidence of restenosis.

Vascular prosthetic devices are often utilized in an effort to maintain vessel patency and prevent restenosis. However, vascular prosthetic devices or patches are often associated with increased thrombogenicity of the PTCA site due to the blood contacting the surfaces of the prosthetic device, and result in occlusion of the vessel. Additionally, synthetic materials used in conventional endovascular prostheses tend to reject coverage by the patient's living tissue, i.e. endothelium, and have collecting surfaces that become thrombogenic sites. Previous biological materials suggested in the art for use in endovascular support have not provided a satisfactory ability to graft to the patient's tissues. Moreover, the body's own repair mechanisms can bring progressive stenotic occlusion due to neointimal fibrosis and hyperplasia. Additionally, an immunological response to foreign material can lead to increased inflammation in response to the prosthetic device.

Systemic therapy aimed at preventing coagulation, a thrombosis locally at the graft site, is often complicated at other sites and produces unwanted, even dangerous side effects. Likewise, systemic treatment with growth mediators or chemotherapeutic agents can produce a hyperplastic or hypoplastic response in tissue not specifically targeted. Existing stent devices, such as dip coated stents, providing locally delivered drugs do not satisfactorily promote grafting or integration of the stent into the patient's endothelium. See for example U.S. Pat. Nos. 5,383,928 and 5,102,417.

Therefore, there exists a need in the art for a device and method for supporting endovascular vessels, which provides local therapy for repairing those blood vessels narrowed or occluded by disease, and which provides a biologically acceptable substrate for grafting to the patient. There is a need for such a device which includes providing local therapy resulting in high local concentrations of therapeutic drugs at the treatment site. The art has sought such an expandable intraluminal vascular support graft, and alternatively an independent arterial-vascular fistula, which prevents recurrence of stenosis, to be utilized to support or replace degenerated vein grafts, coronary arteries, and the peripheral arterial and venous system.

However, prior to the development of the present invention, there has been no expandable intraluminal graft comprised of a biological material which prevents recurrence of restenosis that can also be utilized to deliver drugs locally to the desired location.

SUMMARY OF THE INVENTION

The present invention provides an endovascular support device adapted for local delivery of a therapeutic agent and for minimizing the rate of restenosis. The device has a cylindrical support body having an inside surface and an outside surface. The endovascular support device of the present invention also has at least one layer of pericardial tissue covering at least a portion of the inside surface or the outside surface of the cylindrical support body. The endovascular support device of the present invention is provided with a therapeutic agent disposed on a portion thereof.

BRIEF DESCRIPTIONS OF THE DRAWINGS

DETAILED DESCRIPTION OF TH1E INVENTION

Figure 1:
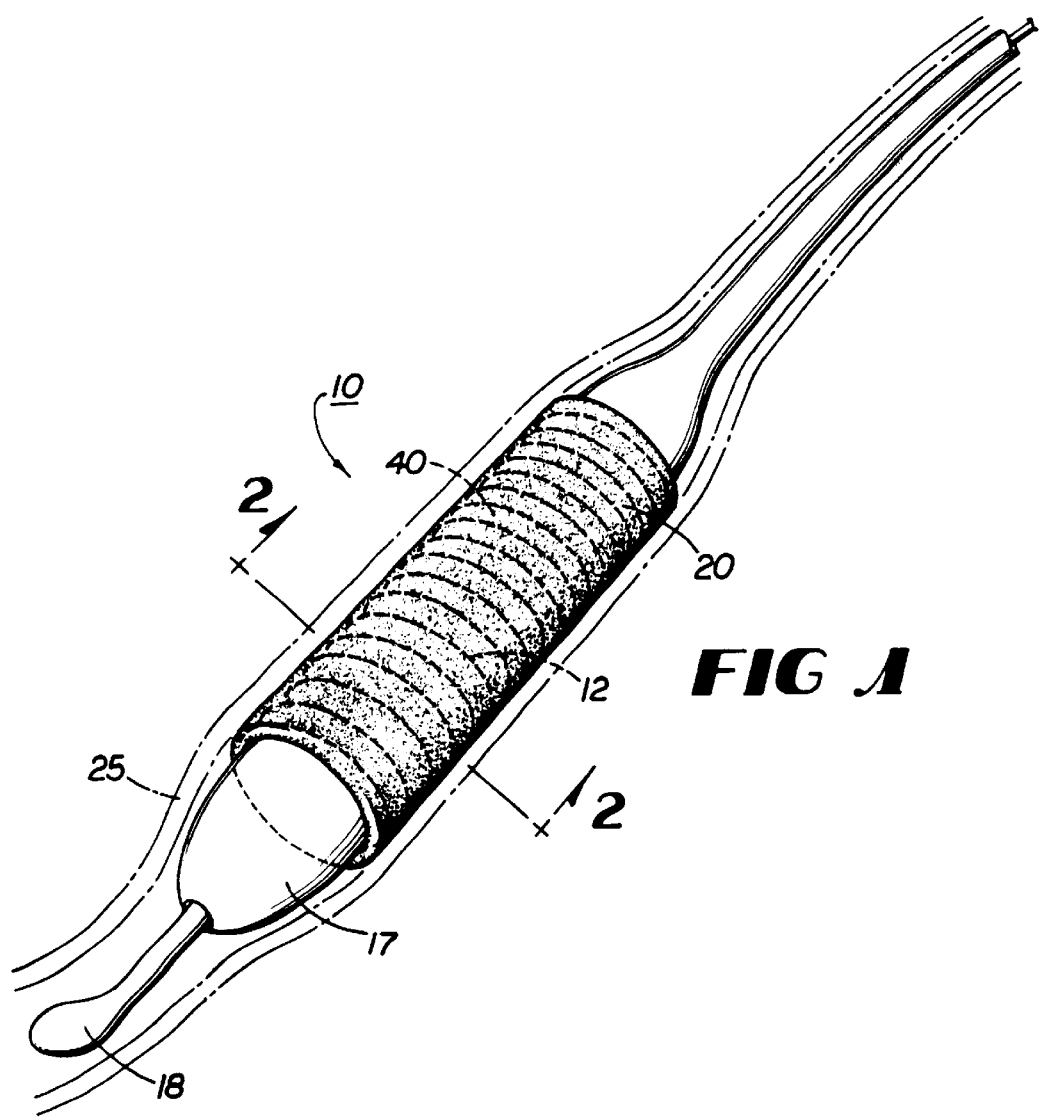
FIG. 1 is a perspective view of the endovascular support device in accordance with one embodiment of the invention positioned on a balloon catheter delivery means inside a vessel.

Referring to FIGS. 1–4, the present invention provides an endovascular support device 10 adapted for local delivery of a therapeutic agent 50 and for minimizing the rate of restenosis. The device 10 has a cylindrical support body 12 having an inside surface 14 and an opposite outside surface 16. The cylindrical support body 12 may be constructed of an expandable flexible wire coil or a tubular mesh of multiple coils or rings. Alternatively, the support body 12 may be constructed of a molded polymer, or similarly rigid substance, or a combination of the two.

An expandable support material can permit precise positioning and maintenance of the device 10 within a bodily vessel 25, with the assistance of an angioplasty balloon 17, as shown in FIG. 1. In common use, a guide wire 18 is inserted within the vessel 25 to the point where endovascular support is desired. An angioplasty balloon 17, or other similar positioning device, carrying the endovascular support device 10 of the present invention, is moved through the vessel 25 along the guide wire 18. At the desired site, the balloon 17 is inflated and the device 10 is positioned against the wails of the vessel. The angioplasty balloon 17 and guide wire 18 are then removed, leaving the device 10 in place to support the vessel 25.

The invention contemplates that the endovascular support device 10 can be used within existing and grafted vessels in a patient. The device 10 may be positioned within a vessel for a variety of purposes, such as for structural support or to occlude an associated aneurysm, for example. The invention also contemplates that the device 10 can be used independently to provide a vascular replacement for ineffective vessels, or as a separate fistula as for dialysis.

Figure 2:
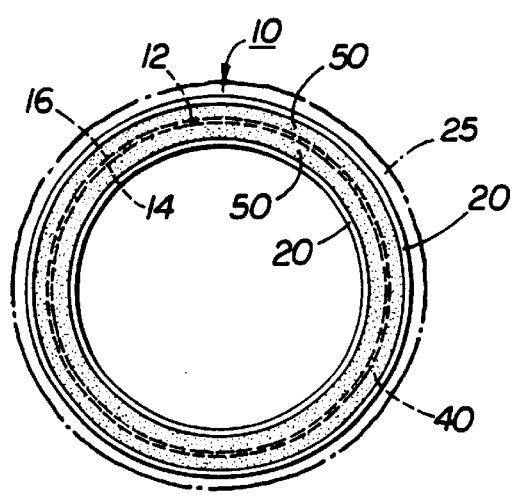
FIG. 2 is a cross section view of the endovascular support device taken along the plane defined by the line 2—2 in FIG. 1, and positioned within a vessel.
Figure 4:
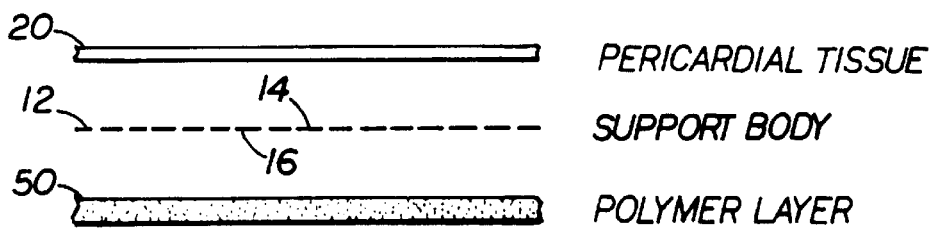
FIG. 4 is a schematic side view of six (FIGS. 4A–4F) alternative embodiments of the endovascular support device of the present invention.

Referring to FIGS. 2 and 4, the endovascular support device 10 of the present invention also has at least one layer of pericardial tissue 20 covering at least a portion of the inside surface 14 or the outside surface 16 of the cylindrical support body 12. The pericardial tissue 20 provides a thin-walled membrane made of biological tissue to promote acceptance and fusion with the patient's blood vessel 25 tissue. The support device 10 surface may have an adjustable thickness by varying the number of tissue 20 layers. The pericardium may be chosen from any mammal but is preferably of porcine, bovine, or human origin.

One skilled in the art will know how to prepare such a pericardial tissue 20 for a homograft or xenograft. For example, porcine pericardium may be retrieved from that surrounding the heart of a sacrificed pig. After shaving the excess fat, the tissue can be immersed in 0.2% glutaraldehyde, which creates permanent strengthening chemical cross-links. The porcine pericardium can then be immersed in porcine albumin solution. When the pericardium is wrapped on the support body 12, it may be adhered to the support body 12 with a biocompatible glue or by careful suturing. The pericardial tissue may be stored in a cold electrolyte solution until used.

Pericardial tissue provides a surprisingly effective biological endovascular support covering. This feature is due, at least in part, to the strength and elasticity of the tissue. The pericardium also has a very low degree of thrombogenicity and is biocompatible with graft recipients. Furthermore, the pericardium serves as an excellent drug delivery means, due to its porosity and high collagen content.

The endovascular support device 10 of the present invention can be provided with at least one therapeutic agent 40 disposed on a portion thereof. By "therapeutic agent" is meant any compound which has a desired pharmacologic effect. By "disposed on" is meant that the therapeutic agent 40 is in contact with at least a portion of the tissue or polymer, described below. For example, the therapeutic agent 40 can be soaked into the tissue or polymer over a period of time, or alternatively, can be injected into a reservoir or cavity created by layers of these materials. The invention contemplates that the device 40 may be made available either presoaked with a therapeutic agent, or provided such that a therapeutic agent is chosen for soaking or injection into the reservoir just prior to placement of the device 10 in the patient.

More specifically, the therapeutic agent 40 can be an anticoagulant, such as D-Phe-Pro-Arg chloromethyl ketone, an RGD peptide-conog compound, heparin, an antithrombin compound, a platelet receptor antagonist, an anti-thrombin antibody, an anti-platelet receptor antibody, aspirin, a prostaglandin inhibitor, a platelet inhibitor or a tick anti-platelet peptide. The therapeutic agent 40 can be a promoter of vascular cell growth, such as a growth factor stimulator, a growth factor receptor agonist, a transcriptional activator, and a translational promoter. Alternatively, the therapeutic agent 40 can be an inhibitor of vascular cell growth, such as a growth factor inhibitor, a growth factor receptor antagonist, a transcriptional repressor, a translational repressor, an antisense DNA, an antisense RNA, a replication inhibitor, an inhibitory antibody, an antibody directed against growth factors, a biflunctional molecule consisting of a growth factor and a cytotoxin, or a bifuinctional molecule consisting of an antibody and a cytotoxin.

The therapeutic agent 40 can be a cholesterol lowerin agent, a vasodlating agent, or other agents which interfere with endogenous vasoactive mechanisms. Additionally, the therapeutic agent 40 can be a smooth muscle inhbitor, such as: an agent that modulates intracelular cacium bindinug proteins; a receptor blocker for contractile agonists; an inhibitor of the sodiun/hydrogen antiporter; a protease inhibitor; a nitrovasodilator; a phosphodiesterase inhibitor, a phenothiazine; a growth factor receptor agonist; an antimitotic agent; an immunosuppressive agent; or a protein sinase inhibitor.

Figure 3:
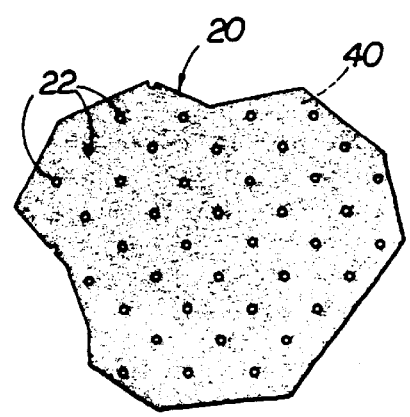
FIG. 3 is a partial cut away view of the pericardial tissue of the endovascular support device with micropores disposed therethrough for delivery of a therapeutic agent.

The therapeutic agent 40 may be disposed on all or a portion of the pericardial tissue 20 to utilize the biological properties of the material to absorb different drugs and to release them slowly after deployment to the adjacent tissue. As seen in FIG. 3, the pericardial tissue 20 can have a plurality of micropores 22 that extend therethrough for more effective delivery of the therapeutic agent 40. The micropores 22 may also be made to extend only partially into one surface of the tissue 20, and not extend entirely therethrough, such that the therapeutic agent 40 can be directed to diffuse primarily in the direction of the micropores. For example, if only one layer of pericardial tissue 20 is employed in the endovascular support device 10, the surface of the pericardial tissue 20 intended to face outward can have a plurality of micropores 22 disposed thereon for delivery of the therapeutic agent 50 primarily toward the adjacent walls of the blood vessel 25, and not toward the interior of the vessel 25. Micropores 22 can be made in the tissue 20 by a variety of means, including by laser incision.

Alternatively, the therapeutic agent 40 may be disposed on all or a portion of a polymer 50, which can be biodegradable and adapted for slow release of the therapeutic agent 40. A polymer 50 laden with one or more therapeutic agents 40 can be positioned on portion of the cylindrical support body 12, wrapped around a portion of the pericardial tissue 20, or imbedded between multiple layers of pericardial tissues 20. Alternatively, the polymer 50 can be constructed so as to form the cylindrical support body 12 itself, then wrapped at least partially with at least one layer of pericardial tissue 20.

A biodegradable polymer 50 such as polylactide, polyanhydride, polyorthoester or polyglycolide, for examnple, can be used. In addition to synthetic polymers, natural polymers can be used, such as amino acid polymers or polysaccharides. The polymer 50 is selected depending on the drug required, the polymer's 50 compatibility with a patient and the ultimate pharmacologic effect desired. For exanple, if the effect need only last a short period, a thin polymer 50 can be used with a limited amount of drug capable of diffusing from the polymer 50 into the arterial wall or lumen of the vessel 25. Alternatively, only the layer closest to the body fluid would contain the therapeutic agent 40. Another alternative would be to use a polymer 50 which is biodegradable over a long period of time. Naturally, the opposite characteristics would be selected for a desired prolonged release.

The characteristics of the particular polymer 50 for these purposes is well known to the skilled artisan or can be determined by reference to standard references, e.g., *Biodegradable Polymers as Drug Delivery Systems*, R. Langer and M. Chasin, Eds., Marcel Dekker Inc., New York, N.Y., USA (1990); Engleberg and Kohn, "Physico-mechanical properties of degradable polymers used in medical applications: a comparative study," *Biomaterials* 12:292–304 (1991); *Controlled Release Delivery Systems*, T. J. Roseman and S. D. Mansdorft Eds., Marcel Dekker Inc., New York, N.Y., USA (1983); and "Controlled Release Technology, Pharmaceutical Applications, ACS Symposium Series, Vol. 348, P. I. Lee and W. R. Good, Eds., American Chemical Society, Washington, D.C., USA (1987).

Generally, the polymer 50 has a therapeutic agent 40 release rate of between about 0.001 $\mu g/cm^2$-min and about 100 $\mu g/cm^2$-min, especially between about 0.01 $\mu cm^2$-min and 10 $\mu g/cm^2$-min. In addition, the polymer 50 generally has a thickness of between about 0.01 mm and 10 mm, especially between about 0.1 mm and 1 mm. As can be appreciated, the device 10 can be comprised of two or more different therapeutic agents 40 or two or more different polymers 50 to obtain a desired effect and release rate. In addition, the polymers 50 can have different solubilities or diffusion characteristics to accomplish non-uniform therapeutic agent 40 release.

Figure 4A:
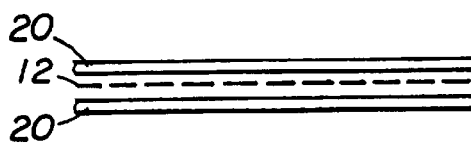
Figure 4B:
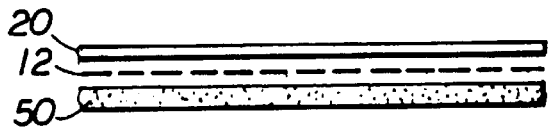
Figure 4C:
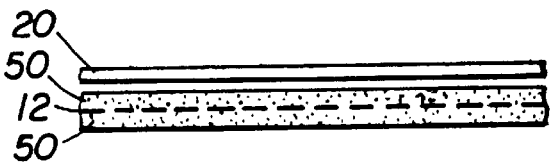

FIGS. 4A–4F show a variety of combinations of the device 10 elements: the support body 12, pericardial tissue 20, and polymer 50, contemplated as different embodiments of the present invention. It is understood from the above description that the therapeutic agent 40 may be disposed on any or all of these elements. As discussed above, the therapeutic agent 40 can be, for example, soaked into the pericardial tissue or polymer, lanlinated on the pericardial tissue or polymer, or injected into a reservoir formed by these materials. FIG. 4A shows one embodiment in which the support body 12 has a pericardial tissue 20 disposed on both the inside surface 14 and outside surface 16 thereof Certainly, the invention contemplates that pericardium tissue 20 can be disposed on either surface alone. FIG. 4B shows the support body 12 covered on the inside surface 14 by a layer of pericardial tissue 20, and covered on the outside surface 16 by a layer of polymer 50. FIG. 4C shows an embodiment in which the support body 12 is covered on the inside surface 14 with a layer of polymer 50 which is in turn covered by a layer of pericardial tissue 20, and the outside surface 16 of the support body 12 is covered by a layer of polymer 50.

Figure 4D:
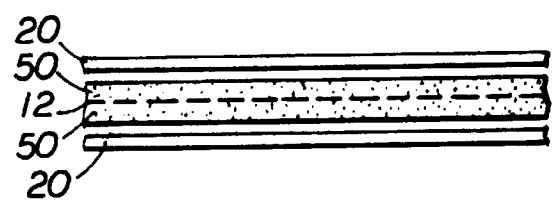
Figure 4E:
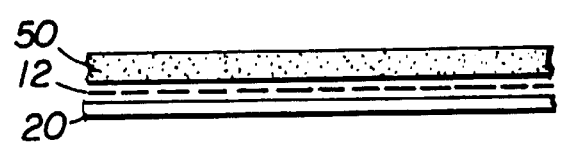
Figure 4F:
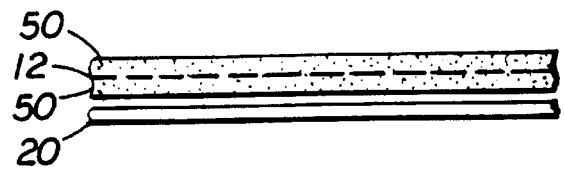

FIG. 4D is the embodiment also shown in cross section in FIG. 2. This embodiment has the support body 12 sandwiched on the inside surface 14 and the outside surface 16 between two layers of polymer 50, which is in turn sandwiched between two layers of pericardial tissue 20. FIG. 4E presents an embodiment wherein the support body 12 is covered on the inside surface 14 by a layer of polymer 50, and on the outside surface 16 by a layer of pericardial tissue 20. Finally, FIG. 4F shows an embodiment having a layer of polymer 50 disposed on the inside surface 14 and a layer of polymer 50 disposed on the outside surface, which is also coated with a layer of pericardial tissue 20.

The present invention also provides methods of using the device 10 to support an endovascular vessel 25 and to locally deliver a therapeutic agent 40 to minimize the rate of restenosis. More particularly, the invention provides methods for treating or preventing a condition associated with coagulation, thrombus formation, fibrosis and restenosis at treated vascular sites.

Throughout this Specification, various publications are referenced. The disclosures of these publications in their entireties are hereby incorporated by reference into this application in order to more fully describe the state of the art to which the invention pertains.

The preceding examples are intended to illustrate, but not limit the invention. While they are typical of those that might be used, other procedures known to those skilled in the art may be alternatively employed. As used herein, "a" means one or more than one, depending upon the context.

What is claimed is:

1. An endovascular support device, comprising:
   a. an expandable cylindrical support body having an inside surface and an opposite outside surface;
   b. at least one layer of pericardial tissue covering at least a portion of at least a selected one of said inside surface or said outside surface of said cylindrical support body; and
   c. a therapeutic agent disposed on a portion of said pericardial tissue, thereby adapting said endovascular support device for local delivery of the therapeutic agent and for minimizing restenosis,
   wherein a surface of the pericardial tissue has a plurality of micropores formed thereon for delivery of the therapeutic agent.

2. The endovascular support device of claim 1, wherein said support body is comprised of material selected from the group consisting of a metal and a plastic polymer.

3. The endovascular support device of claim 1, further comprising at least one layer of a biodegradable polymer on at least a portion of said cylindrical support body, wherein a second therapeutic agent is disposed on at least a portion of said polymer.

4. The endovascular support device of claim 1, wherein said pericardial tissue is selected from the group consisting of porcine, bovine and human pericardial tissue.

5. The endovascular support device of claim 1, wherein the plurality of micropores extend therethrough the pericardial tissue for delivery of said therapeutic agent.

6. The endovascular support device of claim 1, wherein said therapeutic agent is disposed upon said pericardial tissue covering at least a portion of said inside surface of said cylindrical support body.

7. The endovascular support device of claim 1, wherein said therapeutic agent is an anticoagulant selected from the group consisting of D-Phe-Pro-Arg chloromethyl ketone, an RGD peptide-containing compound, heparin, an antithrombin compound, a platelet receptor antagonist, an anti-thrombin antibody, an anti-platelet receptor antibody, aspirin, a prostaglandin inhibitor, a platelet inhibitor and a tick anti-platelet peptide, and combinations thereof.

8. The endovascular support device of claim 1, wherein said therapeutic agent is a promoter of vascular cell growth selected from the group consisting of a growth factor stimulator, a growth factor receptor agonist, a transcriptional activator, and a translational promoter, and combinations thereof.

9. The endovascular support device of claim 1, wherein said therapeutic agent is an inhibitor of vascular cell growth selected from the group consisting of a growth factor inhibitor, a growth factor receptor antagonist, a transcriptional repressor, a translational repressor, an antisense DNA, an antisense RNA, a replication inhibitor, an inhibitory antibody, an antibody directed against growth factors, a bifinctional molecule consisting of a growth factor and a cytotoxin, and a bifiuctional molecule consisting of an antibody and a cytotoxin, and combinations thereof.

10. The endovascular support device of claim 1, wherein said therapeutic agent is selected from the group consisting of a cholesterol-lowering agent, a vasodilating agent, and agents which interfere with endogenous vasoactive mechanisms, and combinations thereof.

11. The endovascular support device of claim 1, wherein said therapeutic agent is a smooth muscle inhibitor selected from the group consisting of an agent that modulates intracellular calcium binding proteins, a receptor blocker for contractile agonists, an inhibitor of the sodium/hydrogen antiporter, a protease inhibitor, a nitrovasodilator, a phosphodiesterase inhibitor, a phenothiazine, a growth factor receptor agonist, an antimitotic agent, an immunosuppressive agent, and a protein kinase inhibitor, and combinations thereof.

12. An endovascular support device, comprising:
   a. an expandable cylindrical support body having an inside surface and an opposite outside surface;
   b. at least one layer of pericardial tissue covering at least a first portion of at least a selected one of said inside surface or said outside surface of said cylindrical support body;
   c. a biodegradable polymer covering at least a second portion of at least a selected one of said inside surface or said outside surface of said cylindrical support body; and
   d. a therapeutic agent disposed on said biodegradable polymer, thereby adapting said endovascular support device for local delivery of the therapeutic agent and for minimizing restenosis, wherein a surface of the pericardial tissue has a plurality of micropores formed thereon for delivery of the therapeutic agent.

13. The endovascular support device of claim 12, wherein at least a portion of said pericardial tissue is disposed on at least a portion of said biodegradable polymer.

14. The endovascular support device of claim 12, wherein at least a portion of said pericardial tissue is disposed between at least a portion of said cylindrical support body and at least a portion of said biodegradable polymer.

15. The endovascular support device of claim 12, wherein a second therapeutic agent is disposed on at least a portion of said pericardial tissue.

16. The endovascular support device of claim 12, wherein said pericardial tissue is selected from the group consisting of porcine, bovine and human pericardial tissue.

17. The endovascular support device of claim 12, wherein the pericardial tissue has a plurality of micropores therethrough for delivery of said therapeutic agent.

18. The endovascular support device of claim 12, wherein said therapeutic agent is an anticoagulant selected from the group consisting of D-Phe-Pro-Arg chloromethyl ketone, an RGD peptide-containing compound, heparin, an antithrombin compound, a platelet receptor antagonist, an antithrombin antibody, an anti-platelet receptor antibody, aspirin, a prostaglandin inhibitor, a platelet inhibitor and a tick anti-platelet peptide, and combinations thereof.

19. The endovascular support device of claim 12, wherein said therapeutic agent is a promoter of vascular cell growth selected from the group consisting of a growth factor stimulator, a growth factor receptor agonist, a transcriptional activator, and a translational promoter, and combinations thereof.

20. The endovascular support device of claim 12, wherein said therapeutic agent is an inhibitor of vascular cell growth selected from the group consisting of a growth factor inhibitor, a growth factor receptor antagonist, a transcriptional repressor, a translational repressor, an antisense DNA, an antisense RNA, a replication inhibitor, an inhibitory antibody, an antibody directed against growth factors, a bifinctional molecule consisting of a growth factor and a cytotoxin, and a bifunctional molecule consisting of an antibody and a cytotoxin, and combinations thereof.

21. The endovascular support device of claim 12, wherein said therapeutic agent is selected from the group consisting of a cholesterol-lowering agent, a vasodilating agent, and agents which interfere with endogenous vasoactive mechanisms, and combinations thereof.

22. The endovascular support device of claim 12, wherein said therapeutic agent is a smooth muscle inhibitor selected from the group consisting of an agent that modulates intracellular calcium binding proteins, a receptor blocker for contractile agonists, an inhibitor of the sodium/hydrogen antiporter, a protease inhibitor, a nitrovasodilator, a phosphodiesterase inhibitor, a phenothiazine, a growth factor receptor agonist, an antimitotic agent, an immunosuppressive agent, and a protein kinase inhibitor, and combinations thereof.

23. An endovascular support device, comprising:
   a. an expandable cylindrical support body having an inside surface and an opposite outside surface;
   b. a first pericardial tissue covering at least a first portion of at least a selected one of said inside surface or said outside surface of said cylindrical support body;
   c. a second pericardial tissue covering at least a second portion of at least a selected one of said inside surface or said outside surface of said cylindrical support body; and
   d. at least one therapeutic agent disposed in a reservoir between said first pericardial tissue and said second pericardial tissue, thereby adapting said endovascular support device for local delivery of the therapeutic agent and for minimizing restenosis,
wherein a surface of the pericardial tissue has a plurality of micropores formed thereon for delivery of the therapeutic agent.

24. The endovascular support device of claim 23, further comprising a biodegradable polymer on at least a portion of said cylindrical support body, wherein a second therapeutic agent is disposed on at least a portion of said biodegradable polymer.

25. The endovascular support device of claim 23, wherein said pericardial tissue is selected from the group consisting of porcine, bovine and human pericardial tissue.

26. The endovascular support device of claim 23, wherein the plurality of micropores extend therethrough the pericardial tissue for delivery of said therapeutic agent.

27. A method of supporting an endovascular vessel and locally delivering a therapeutic agent and minnmizing restenosis, comprising inserting in the vessel an endovascular support device comprising:
   a. an expandable cylindrical support body having an inside surface and an opposite outside surface;
   b. at least one layer of pericardial tissue covering at least a portion of at least a selected one of said inside surface or said outside surface of said cylindrical support body; and
   c. a therapeutic agent disposed on at least a portion of said pericardial tissue, thereby supporting the endovascular vessel and locally delivering the therapeutic agent and minimizing restenosis,
wherein a surface of the pericardial tissue has a plurality of micropores formed thereon for delivery of the therapeutic agent.

28. A method of supporting an endovascular vessel and locally delivering a therapeutic agent and minimizing restenosis, comprising the steps of:

a. inserting an endovascular support device in the vessel, said support device comprising an expandable cylindrical support body having an inside surface and an opposite outside surface, at least one layer of pericardial tissue covering at least a portion of at least a selected one of said inside surface or said outside surface of said cylindrical support body, and a therapeutic agent disposed on at least a portion of said pericardial tissue, wherein a surface of the pericardial tissue has a plurality of micropores formed thereon for delivery of the therapeutic agent; and b. expanding said support device within the vessel, thereby supporting the endovascular vessel and locally delivering the therapeutic agent and minimizing restenosis.

* * * * *